(12) United States Patent
Whitehurst et al.

(10) Patent No.: US 8,588,917 B2
(45) Date of Patent: Nov. 19, 2013

(54) FULLY IMPLANTABLE NEUROSTIMULATOR FOR AUTONOMIC NERVE FIBER STIMULATION AS A THERAPY FOR URINARY AND BOWEL DYSFUNCTION

(75) Inventors: Todd K. Whitehurst, Sherman Oaks, CA (US); James P. McGivern, Stevenson Ranch, CA (US); Carla M. Mann, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/493,753

(22) Filed: Jun. 11, 2012

(65) Prior Publication Data

US 2012/0245652 A1      Sep. 27, 2012

Related U.S. Application Data

(63) Continuation of application No. 11/373,756, filed on Mar. 10, 2006, now Pat. No. 8,214,048, which is a continuation of application No. 09/929,596, filed on Aug. 13, 2001, now Pat. No. 7,054,689.

(60) Provisional application No. 60/226,332, filed on Aug. 18, 2000.

(51) Int. Cl.
*A61N 1/00*       (2006.01)
*A61B 5/103*     (2006.01)

(52) U.S. Cl.
USPC .............................. 607/40; 607/41; 600/587

(58) Field of Classification Search
USPC ...................... 607/40–41; 600/587
See application file for complete search history.

(56) References Cited

U.S. PATENT DOCUMENTS

| 3,236,240 A | 2/1966 | Bradley |
| 3,628,538 A | 12/1971 | Vincent et al. |

(Continued)

FOREIGN PATENT DOCUMENTS

| EP | 02/45547 B1 | 8/1990 |
| WO | WO 97/18857 A1 | 5/1997 |

(Continued)

OTHER PUBLICATIONS

Official Communication, U.S. Appl. No. 09/929,596, mailed Sep. 12, 2003.

(Continued)

*Primary Examiner* — Nicole F Lavert
(74) *Attorney, Agent, or Firm* — Frommer Lawrence & Haug LLP; Patrick R. Turner

(57) ABSTRACT

An implantable stimulator(s), small enough to be located near or adjacent to an autonomic nerve(s) innervating urinary and/or gastrointestinal structures, uses a power source/storage device, such as a rechargeable battery. Periodic recharging of such a power source/storage device is accomplished, for example, by inductive coupling with an external appliance. The small stimulator provides a means of stimulating a nerve(s) or other tissue when desired, without the need for external appliances during the stimulation session. When necessary, external appliances are used for the transmission of data to and/or from the stimulator(s) and for the transmission of power, if necessary. In a preferred embodiment, the system is capable of open- and closed-loop operation. In closed-loop operation, at least one implant includes at least one sensor, and the sensed condition is used to adjust stimulation parameters.

14 Claims, 6 Drawing Sheets

(56) References Cited

U.S. PATENT DOCUMENTS

| | | | |
|---|---|---|---|
| 3,646,940 A | | 3/1972 | Timm et al. |
| 3,650,275 A | * | 3/1972 | Von Der Mozel ............. 607/76 |
| 3,650,276 A | | 3/1972 | Burghele et al. |
| 3,667,477 A | | 6/1972 | Susset et al. |
| 3,699,970 A | | 10/1972 | Brindley et al. |
| 3,870,051 A | | 3/1975 | Brindley |
| 4,106,511 A | | 8/1978 | Erlandsson |
| 4,153,059 A | | 5/1979 | Fravel et al. |
| 4,387,719 A | | 6/1983 | Plevnik et al. |
| 4,406,288 A | | 9/1983 | Horwinski et al. |
| 4,431,001 A | | 2/1984 | Hakansson et al. |
| 4,569,351 A | | 2/1986 | Tang |
| 4,585,005 A | | 4/1986 | Lue et al. |
| 4,607,639 A | | 8/1986 | Tanagho et al. |
| 4,703,755 A | | 11/1987 | Tanagho et al. |
| 4,739,764 A | | 4/1988 | Lue et al. |
| 4,771,779 A | | 9/1988 | Tanagho et al. |
| 5,040,533 A | * | 8/1991 | Fearnot ............................ 607/22 |
| 5,094,242 A | | 3/1992 | Gleason et al. |
| 5,193,539 A | | 3/1993 | Schulman et al. |
| 5,193,540 A | | 3/1993 | Schulman et al. |
| 5,199,430 A | | 4/1993 | Fang et al. |
| 5,312,439 A | | 5/1994 | Loeb |
| 5,314,458 A | | 5/1994 | Najafi et al. |
| 5,324,316 A | | 6/1994 | Schulman et al. |
| 5,358,514 A | | 10/1994 | Schulman et al. |
| 5,405,367 A | | 4/1995 | Schulman et al. |
| 5,562,717 A | | 10/1996 | Tippey et al. |
| 5,571,148 A | | 11/1996 | Loeb et al. |
| 5,702,428 A | * | 12/1997 | Tippey et al. .................. 607/41 |
| 5,833,595 A | | 11/1998 | Lin |
| 5,834,051 A | * | 11/1998 | Woloszko et al. ........... 427/2.24 |
| 5,957,965 A | | 9/1999 | Moumane et al. |
| 5,984,854 A | | 11/1999 | Ishikawa et al. |
| 6,026,326 A | | 2/2000 | Brady |
| 6,051,017 A | | 4/2000 | Loeb et al. |
| 6,055,456 A | | 4/2000 | Gerber |
| 6,061,596 A | * | 5/2000 | Richmond et al. .............. 607/41 |
| 6,086,549 A | | 7/2000 | Neese et al. |
| 6,104,955 A | | 8/2000 | Bourgeois |
| 6,104,960 A | | 8/2000 | Duysens et al. |
| 6,185,452 B1 | | 2/2001 | Schulman et al. |
| 6,192,279 B1 | | 2/2001 | Barreras et al. |
| 6,205,359 B1 | | 3/2001 | Boveja |
| 6,208,894 B1 | | 3/2001 | Schulman et al. |
| 6,240,316 B1 | | 5/2001 | Richmond et al. |
| 6,354,991 B1 | | 3/2002 | Gross et al. |
| 6,360,750 B1 | | 3/2002 | Gerber et al. |
| 6,393,323 B1 | | 5/2002 | Sawan et al. |
| 6,407,308 B1 | | 6/2002 | Roe et al. |
| 6,505,074 B2 | | 1/2003 | Boveja |
| 6,652,449 B1 | * | 11/2003 | Gross et al. ..................... 600/30 |
| 6,658,297 B2 | | 12/2003 | Loeb |
| 6,735,474 B1 | | 5/2004 | Loeb et al. |
| 7,054,689 B1 | | 5/2006 | Whitehurst |
| 8,214,048 B1 | | 7/2012 | Whitehurst |

FOREIGN PATENT DOCUMENTS

| | | |
|---|---|---|
| WO | WO 98/37926 A1 | 9/1998 |
| WO | WO 98/43700 A1 | 10/1998 |
| WO | WO 98/43701 A1 | 10/1998 |
| WO | WO 00/01320 A3 | 1/2000 |
| WO | WO 00/19939 A1 | 4/2000 |
| WO | WO 00/25859 A1 | 5/2000 |
| WO | WO 01/52729 A2 | 7/2001 |
| WO | WO 01/54767 A1 | 8/2001 |
| WO | WO 01/60445 A2 | 8/2001 |

OTHER PUBLICATIONS

Official Communication, U.S. Appl. No. 09/929,596, mailed May 6, 2004.
Official Communication, U.S. Appl. No. 09/929,596, mailed Dec. 15, 2004.
Official Communication, U.S. Appl. No. 09/929,596, mailed Jun. 7, 2005.
Official Communication, U.S. Appl. No. 11/373,756, mailed Jun. 30, 2008.
Official Communication, U.S. Appl. No. 11/373,756, mailed Jan. 8, 2009.
Official Communication, U.S. Appl. No. 11/373,756, mailed Apr. 16, 2009.
Official Communication, U.S. Appl. No. 11/373,756, mailed Nov. 3, 2009.
Official Communication, U.S. Appl. No. 11/373,756, mailed Feb. 19, 2010.
Official Communication, U.S. Appl. No. 11/373,756, mailed Jul. 21, 2010.
Official Communication, U.S. Appl. No. 11/373,756, mailed Jan. 5, 2011.
Official Communication, U.S. Appl. No. 11/373,756, mailed Mar. 21, 2011.
Cameron, et al., "Micromodular Implants to Provide Electrical Stimulation of Paralyzed Muscles and Limbs," IEEE Transactions on Biomedical Engineering, vol. 44, No. 9 (Sep. 1997), pp. 781-790.
Crocker et al., "Transcutaneous Electrical Nerve Stimulation in Urinary Retention," Southern Medical Journal, vol. 78, No. 12 (1985), pp. 1515-1516.
Fall et al., "Electrical Stimulation. A Physiologic Approach to the Treatment of Urinary Incontinence," Urol. Clin. North Am., vol. 18, No. 2 (May 1991), pp. 393-407.
IC in the News! ICN Feature Stories; printed Mar. 2, 2000; pp. 1-7. Lower Back Pain, Neck Pain, Arthritis—Pain Management & Muscle Stimulation—Ottawa . . . ; printed Mar. 2, 2000; p. 1.
Malouf, et al., "Permanent Sacral Nerve Stimulation for Fecal Incontinence," Ann Surg., vol. 232, No. 1 (Jul. 2000, pp. 143-148.
McGuire, et al., "Treatment of Motor and Sensory Detrusor Instability by Electrical Sfirriulation," Journal of Urology, vol. 129, No. 1 (1983), pp. 78-79.
Medtronic InterStim Urinary Control—FAQ's; printed Mar. 2, 2000; pp. 1-7.
Medtronic's InterStim Therapy for Urinary Co . . . : For People with Bladder Control Problem; printed Mar. 2, 2000; pp. 1-2.
Medtronic's InterStim Therapy for Urinary Control for Health Care Professionals; printed Mar. 2, 2000; pp. 1-2.
Merrill, "The Treatment of Detrusor Incontinence by Electrical Stimulation," J. Urol., vol. 122, No. 4 (Oct. 1979), pp. 515-517.
Merrill, et al., "Urinary Incontinence. Treatment with Electrical Stimulation of the Pelvic Floor," Urology, vol. 5, No. 1 (Jan. 1975), pp. 67-72.
Murray, Letter re: "Treatment of Motor and Sensory Detrusor Instability by Electrical Stimulation" and re: The Neurophysiological Basis of Bladder Inhibition in Response to Intravaginal Eiectrical Stimulation, Journal of Urology, vol. 131, No. 2 (1984), p. 356.
Ohlsson, et al., "Effects of External and Direct Pudendal Nerve Maximal Electrical Stimulation in the Treatment of the Uninhibited Overactive Bladder," British Journal of Urology, Vol, 64 (1989), pp. 374-380.
Our Products: Incontinence Therapies: Innova® PFS; printed Mar. 2, 2000; pp. 1-2.
Our Products: Incontinence Therapies; printed Mar. 2, 2000; pp. 1-2.
Sawan, et al., "Computerized Transcutaneous Control of a Multichannel implantable Urinary Prosthesis," IEEE Transactions on Biomedical Engineering, vol. 39, No. 6 (Jun. 1, 1992), pp. 600-609.
Schmidt, et al., "Sacral Nerve Stimulation for Treatment of Refractory Urinary Urge Incontinence. Sacral Nerve Stimulation Study Group," J. Urol., vol. 162, No. 2 (Aug. 1999), pp. 352-357.
Shafik, et al., "Sacral Root Stimulation for Controlled Defecation," Eur. Surg. Res., vol. 27, No. 1 (1995), pp. 63-68.
Shaker, et al. "Sacral Nerve Root Neuromodulation: an Effective Treatment for Refractory Urge Incontinence," J. Urol. vol. 159, No. 5 (May 1998), pp. 1516-1519.
Sundin, et al., Detrusor Inhibition Induced from Mechanical Stimulation of the Anal Region and from Electrical Stimulation of Pudendal Nerve Afferents, Investigative Urology, vol. 11, No. 5 (1974), pp. 374-378.

(56) References Cited

OTHER PUBLICATIONS

Teague, et al., "Electric Pelvic Floor Stimulation. Mechanism of Action," Invest. Urol. vol. 15, No. 1 (Jul. 1977), pp. 65-69.
UroSurge—SANS (Stoller Afferent Nerve Stimulation) Device; printed Mar. 2, 2000; pp. 1-5.
UroSurge—SANS 2; printed Mar. 2, 2000; pp. 1-2.
UroSurge—SANS AUA Abstract; printed Mar. 2, 2000; pp. 1-2.
Vodusek, et al., "Detrusor Inhibition Induced by Stimulation of Pudendal Nerve Afferents," Neurourology and Urodynamics, vol. 5 (1986), pp. 381-389.
Vodusek, et al., "Detrusor Inhibition on Selective Pudendal Nerve Stimulation in the Perineum," Neurourology and Urodynamics, vol. 6 (1988) pp. 389-393.
What is Medtronic InterStim Therapy for Urinary Control; printed Mar. 2, 2000; pp. 1-2.

\* cited by examiner ic
FULLY IMPLANTABLE NEUROSTIMULATOR FOR AUTONOMIC NERVE FIBER STIMULATION AS A THERAPY FOR URINARY AND BOWEL DYSFUNCTION The present application is a continuation U.S. application Ser. No. 11/373,756, filed Mar. 10, 2006 (now allowed), which is a continuation of U.S. application Ser. No. 09/929,596, filed Aug. 13, 2001 now U.S. Pat. No. 7,054,689, issued May 30, 2006, which application claims the benefit of Provisional Application Ser. No. 60/226,332, filed Aug. 18, 2000. All of which are herein incorporated by reference in their entireties.

FIELD OF THE INVENTION

The present invention generally relates to implantable stimulator systems, and more particularly relates to an implantable stimulator system utilizing one or more implantable microstimulators for treating urinary dysfunction and/or bowel dysfunction.

BACKGROUND OF THE INVENTION

The most prevalent form of urinary dysfunction is incontinence. Urinary Incontinence is a clinical condition characterized by failure to hold urine in the bladder under normal conditions of pressure and filling. The most common forms of the disorder can arise from either a failure of muscles around the bladder neck and urethra to maintain closure of the urinary outlet (so-called stress incontinence) or from abnormally heightened commands from the spinal cord to the bladder that produce unanticipated bladder contractions (so-called urge incontinence). Many patients exhibit a grouping of symptoms suggesting that these disorders may occur simultaneously in the same individual (so-called mixed incontinence).

It is well known in the art that electrical stimulation in the region of the pelvic floor can decrease the severity of urinary incontinence. The improvement is believed to be attained through at least three mechanisms: (1) by changing the reflex thresholds of the bladder muscles responsible for bladder emptying, (2) by strengthening the muscles that maintain closure on the bladder outlet, and (3) by changing the state of the neural pathways, musculature and/or bladder during and beyond the period of stimulus application.

The therapies currently available for urinary incontinence have generally been directed at improving muscle condition, as disclosed, e.g., in applicant's prior document WO97/18857 (PCT/US96/18680), published 29 May 1997. Bladder hyperreflexia and detrusor instability have proven more difficult to treat. However, evidence in the art suggests that many individuals with these conditions can be improved by stimulating peripheral nerves or nerve roots continuously or intermittently to modulate transmission of excitatory nerve signals to the bladder muscles.

Several external and implantable approaches have been used to stimulate the nerves supplying the bladder and pelvic region in order to decrease the episodic incidences of unintentional bladder emptying. Those that strengthen periurethral muscles have usually employed vaginal or anal electrode assemblages to stimulate muscle contractions repeatedly. These methods are limited in their portability and are often poorly accepted by patients because they are inconvenient and often associated with unpleasant skin sensations. Further, the methods are inadequate for the treatment of urge incontinence in which continual electrical stimulation is commonly needed to diminish or inhibit the heightened reflexes of bladder muscles.

The sacral nerve roots exert significant neural control over the process of urination. Neurostimulation of sacral nerve roots, in particular the S3 sacral nerve roots, has been applied therapeutically in patients with urinary incontinence. Sacral nerve root stimulation has also been applied to promote urination in patients who are unable to initiate voiding through normal neural mechanisms.

For the treatment of urge incontinence, surgically implanted stimulators under battery or radio-frequency control have been described in the art. These stimulators have different forms, but are usually comprised of an implantable control module to which is connected a series of leads that must be routed to nerve bundles in either the sacral roots emanating from the spinal cord, or the nerves supplying muscles, skin or other structures in the pelvic region. The implantable devices are relatively large and expensive. In addition, they require significant surgical procedures for placement of electrodes, leads, and processing units. These devices may also require an external apparatus that needs to be strapped or otherwise affixed to the skin. Thus, their use has generally been confined to patients with severe symptoms and the capacity to finance the surgery.

These same types of therapies have been used to treat fecal incontinence and other bowel dysfunctions, with the same drawbacks. For instance, neurostimulation of sacral nerve roots has been investigated for therapeutic application in patients with fecal incontinence. Sacral nerve root stimulation has also been applied to promote defecation in patients who are unable to initiate voiding through normal neural mechanisms. As with known treatments for urinary dysfunction, currently available devices have several drawbacks, such as size (of internal and/or external components), discomfort, inconvenience, complex surgical procedures, and/or only acute or intermittent use. Other devices used for both urinary and bowel dysfunctions require that a needle electrode(s) be inserted through the skin during stimulation sessions. These devices may only be used acutely, and may cause significant discomfort.

Recently, small, implantable microstimulators have been introduced that can be injected into soft tissues through a cannula or needle. What is needed is a way to effectively use such small, fully implantable, chronic neurostimulators for the purpose of treating urinary and/or bowel dysfunction.

BRIEF SUMMARY OF THE INVENTION

The invention disclosed and claimed herein addresses the above and other needs and provides means and systems for chronically stimulating one or more parasympathetic nerves, such as a sacral nerve root(s) and/or sacral spinal nerve(s) with a miniature implantable neurostimulator(s) that can be implanted with a minimal surgical procedure.

The sacral nerve roots lie within the spinal column, and the sacral spinal nerves exit the sacral spinal column in the posterior pelvis. To treat urinary and/or bowel dysfunction, a miniature implantable electrical stimulator, such as a stimulator similar to a Bionic Neuron (also referred to as a BION™ microstimulator) may be implanted via a minimal surgical procedure (e.g., injection or small incision) in the spinal column in an epidural location for stimulation of a sacral root(s) and/or in the posterior pelvis for stimulation of a sacral spinal nerve(s). A single microstimulator may be implanted, or two or more microstimulators may be implanted to achieve greater stimulation of additional branches of the sacral roots and/or spinal nerves. For instance, a microstimulator(s) may be implanted adjacent to the third sacral nerve root (i.e., S3), and/or the second and/or fourth sacral nerve roots (i.e., S2, S4). Alternatively or additionally, a microstimulator(s) may be implanted adjacent to one or more of the sacral spinal nerves, or microstimulators may be implanted adjacent to one or more sacral nerve roots and one or more sacral spinal nerves.

According to one embodiment of the invention, incontinence and related dysfunctions may be treated with stimulation to decrease excitement of the parasympathetic input to the pelvic region; high-frequency electrical stimulation of parasympathetic fibers is likely to produce such inhibition. According to another embodiment of the invention, the stimulation can increase excitement of the sympathetic input to the pelvic region; low-frequency electrical stimulation of sympathetic fibers is likely to produce such excitement.

Stimulation may also be used to promote urination or defecation in patients unable to properly initiate these actions themselves. According to one such embodiment, low frequency stimulation is used to increase excitement of the parasympathetic input to the pelvic region. According to another embodiment, high frequency stimulation is used to inhibit sympathetic input to the pelvic region.

The neurostimulator also includes a means of stimulating a nerve either intermittently or continuously. Specific stimulation parameters may provide therapeutic advantages for various forms of urinary and bowel dysfunction.

The microstimulator used with the present invention preferably possesses one or more of the following properties:
- at least two electrodes for applying stimulating current to surrounding tissue;
- electronic and/or mechanical components encapsulated in a hermetic package made from biocompatible material(s);
- an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the microstimulator; and
- a form factor making the microstimulator implantable via a minimal surgical procedure.

A microstimulator may operate independently, or in a coordinated manner with other implanted devices, or with external devices. In addition, a microstimulator may incorporate means for sensing a patient's condition, which it may then use to control stimulation parameters in a closed loop manner. According to one embodiment of the invention, the sensing and stimulating means are incorporated into a single microstimulator. According to another embodiment of the invention, a sensing means communicates sensed information to at least one microstimulator with stimulating means.

Thus, the present invention provides a therapy for urinary and/or bowel dysfunction that utilizes one or more miniature neurostimulators and is minimally invasive. The simple implant procedure results in minimal surgical time and possible error, with associated advantages over known treatments in terms of reduced expense and opportunity for infection or other complications. Other advantages, inter alia, of the present invention include the system's monitoring and programming capabilities, the power source, storage, and transfer mechanisms, the activation of the device by the patient or clinician, the system's open and closed-loop capabilities and closed-loop capabilities coupled with sensing a need for and/or response to treatment, coordinated use of one or more stimulators, and the small size of the stimulator.

BRIEF DESCRIPTION OF THE DRAWINGS

The above and other aspects, features, and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
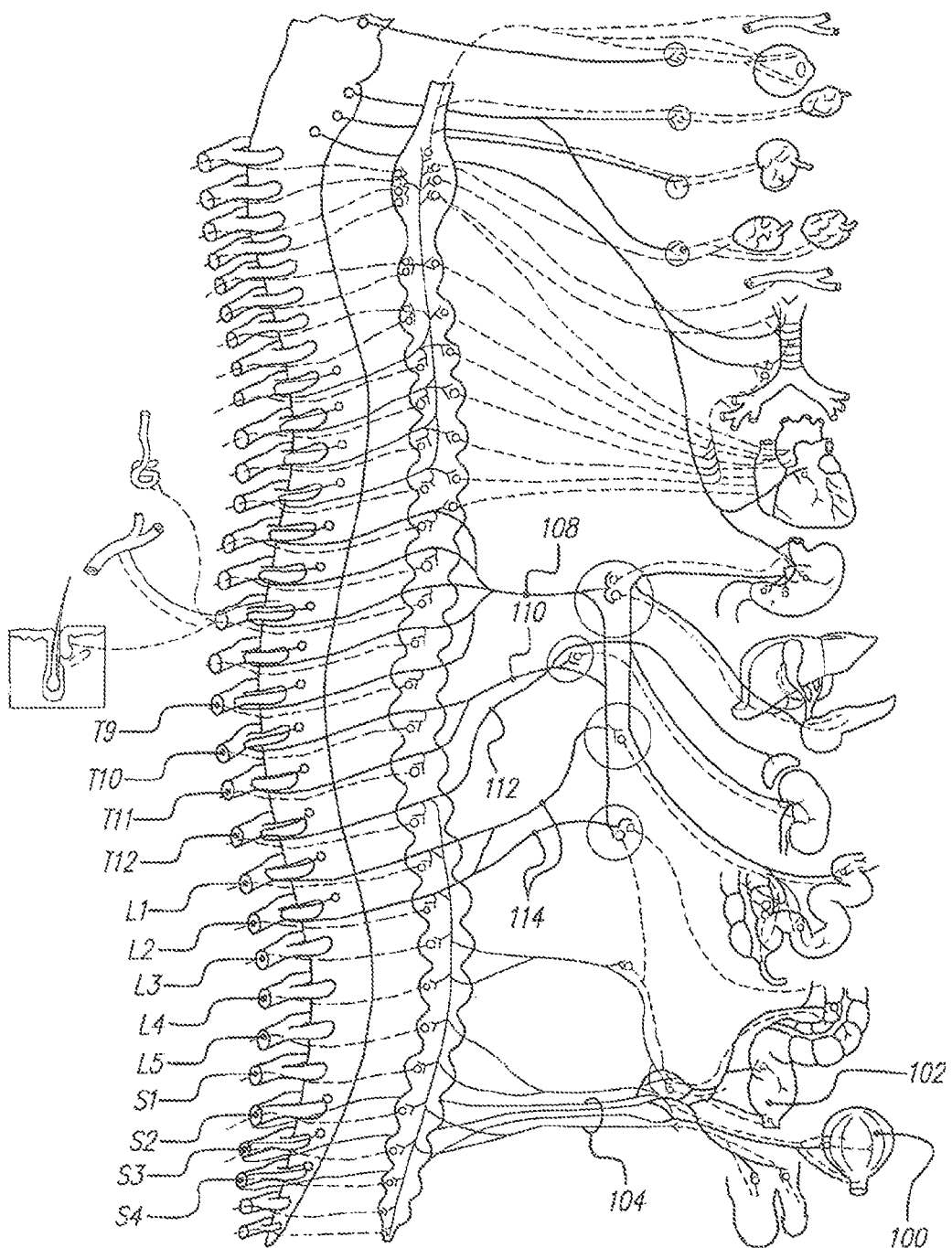
FIG. 1 is a schema of the autonomic nervous system and the anatomy the autonomic nerves influences.
Figure 2:
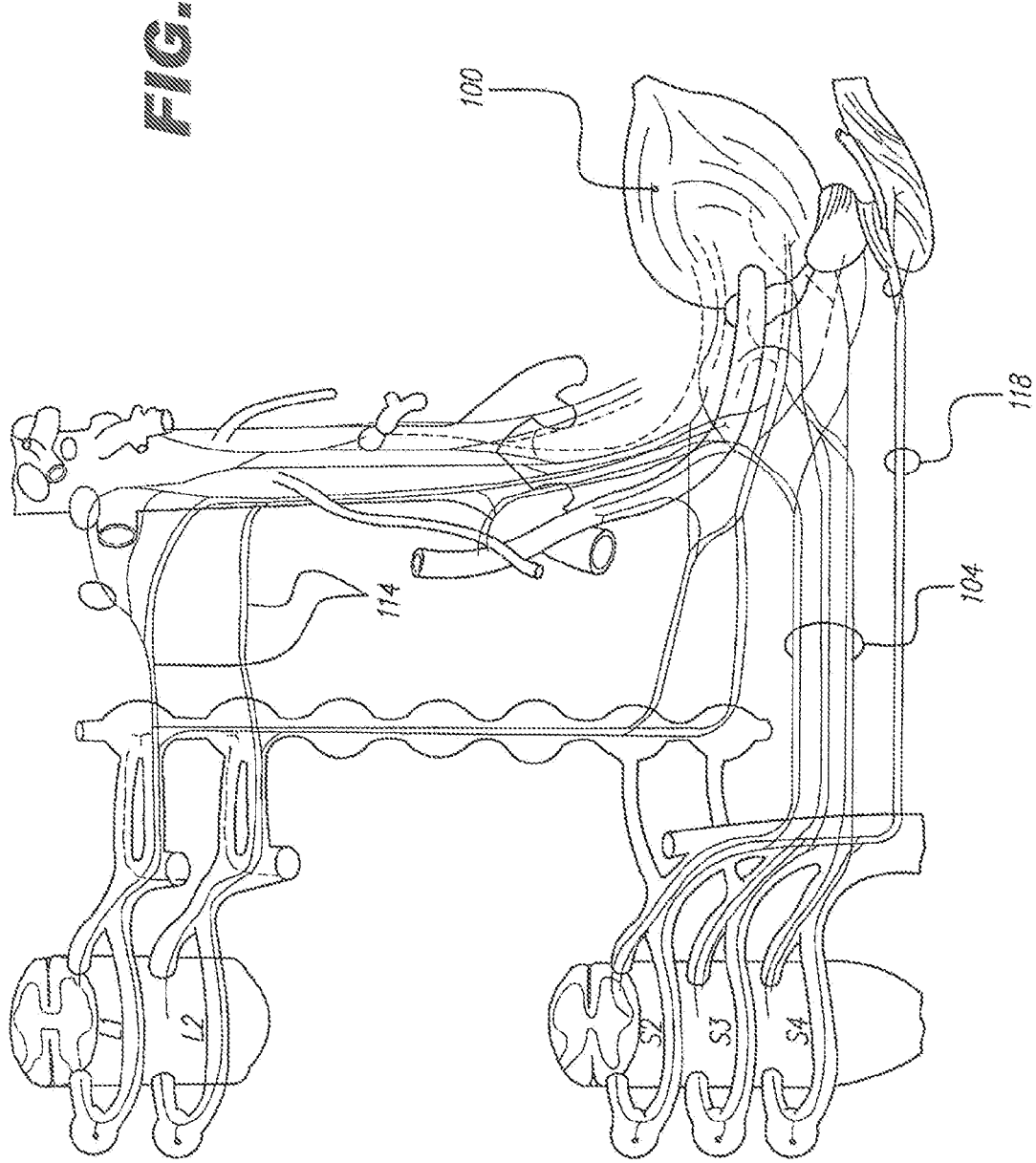
FIG. 2 illustrates the innervation of the urinary bladder and lower ureter and a stimulation system of the present invention.
Figure 3:
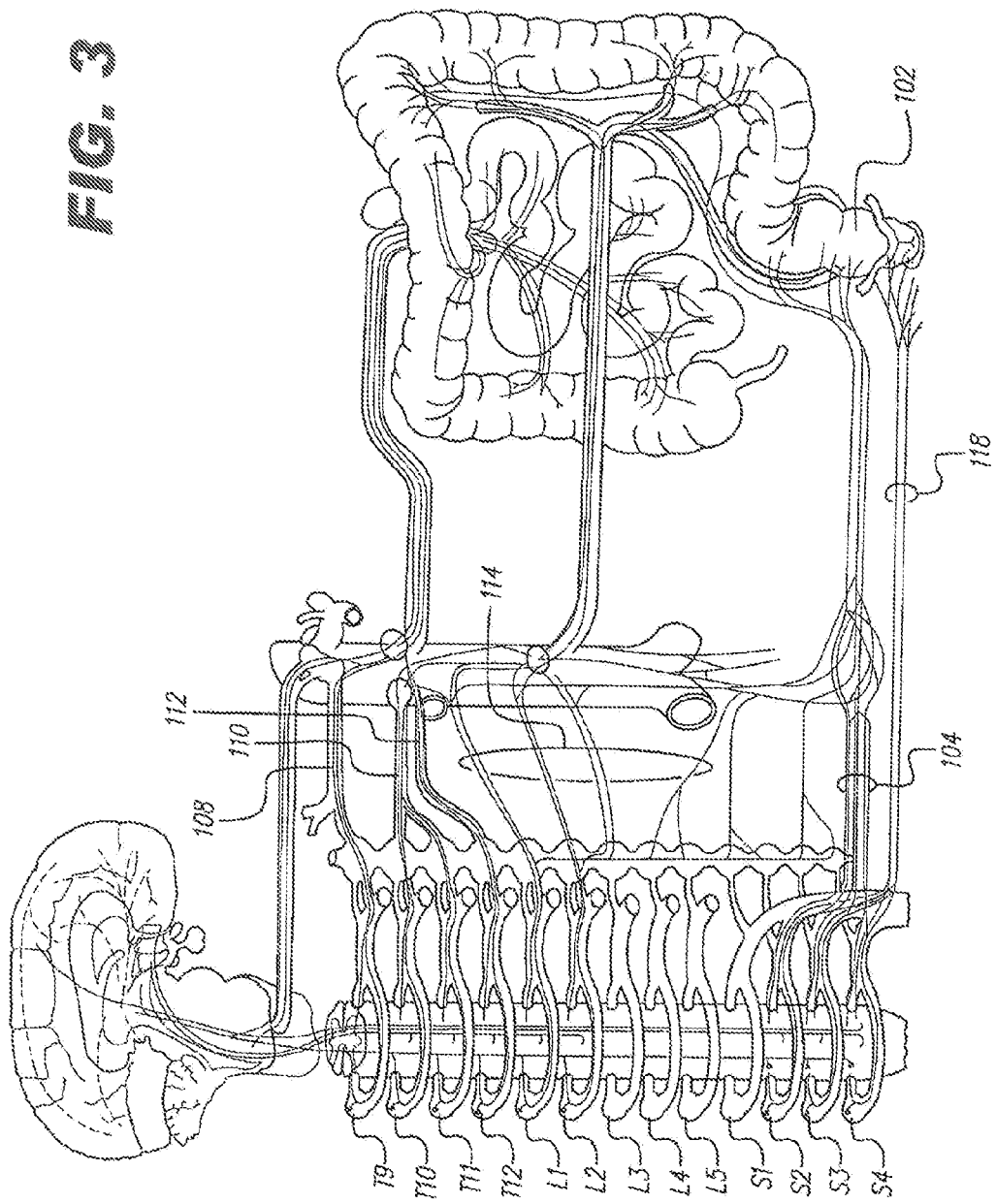
FIG. 3 illustrates the innervation of the small and large intestines.

FIG. 1 is a schematic representation of the sympathetic and parasympathetic fibers of the autonomic nervous system and the anatomical structures they affect. FIG. 2 depicts the nerves innervating the urinary bladder 100 and lower ureter and FIG. 3 depicts the nerves innervating the small and large intestines.

Under normal conditions, sympathetic input to urinary bladder 100 and associated structures inhibits urination, and parasympathetic input allows the initiation and continuation of urination until completion. Since these systems are antagonistic, sympathetic and parasympathetic inputs are generally not both strongly activated simultaneously. Similarly, sympathetic input to the rectum 102 and associated structures inhibits defecation, and parasympathetic input causes defecation to begin. This parasympathetic input originates at the sacral part of the spinal cord (e.g., S2, S3, and S4) and is carried by the pelvic splanchnic nerves 104 to the various innervating nerve branches. Sympathetic input to the pelvis originates at the thoracolumbar part of the spinal cord (e.g., T9 through T12, L1 through L4) and is carried by the greater splanchnic nerve 108, lesser splanchnic nerve 110, least splanchnic nerve 112, lumbar splanchnic nerves 114, and sacral splanchnic nerves, to innervating nerve branches, such as the hypogastric nerves, the superior hypogastric plexus, and the inferior hypogastric plexus.

As indicated above, the present invention is directed to treating urinary and bowel dysfunction using one or more small, implantable neurostimulators, referred to herein as "microstimulators". The microstimulators of the present invention are preferably similar to the type referred to as BION™ devices. The following documents describe various features and details associated with the manufacture, operation, and use of BION implantable microstimulators, and are all incorporated herein by reference:

| Patent/ Publication No. | Filing/Publication Date | Title |
| --- | --- | --- |
| U.S. Pat. No. 5,193,539 | Issued: Mar. 16, 1993 | Implantable Microstimulator |
| U.S. Pat. No. 5,193,540 | Issued: Mar. 16, 1993 | Structure and Method of Manufacture of an Implantable Microstimulator |
| U.S. Pat. No. 5,312,439 | Issued: May 17, 1994 | Implantable Device Having an Electrolytic Storage Electrode |
| U.S. Pat. No. 5,324,316 | Issued: Jun. 28, 1994 | Implantable Microstimulator |
| U.S. Pat. No. 5,405,367 | Issued: Apr. 11, 1995 | Structure and Method of Manufacture of an Implantable Microstimulator |
| WO 98/37926 | Published: Sept. 03, 1998 | Battery-Powered Patient Implantable Device |
| WO 98/43700 | Published: Oct. 08, 1998 | System of Implantable Devices For Monitoring and/or Affecting Body Parameters |
| WO 98/43701 | Published: Oct. 08, 1998 | System of Implantable Devices For Monitoring and/or Affecting Body Parameters |
| U.S. Pat. No. 6,051,017 | Issued: Apr. 18, 2000 | Improved Implantable Microstimulator and Systems Employing Same |
| | Published: Sept., 1997 | Micromodular Implants to Provide Electrical Stimulation of Paralyzed Muscles and Limbs, by Cameron, et al., published in IEEE Transactions on Biomedical Engineering, Vol. 44, No. 9, pages 781-790. |

Figure 4:
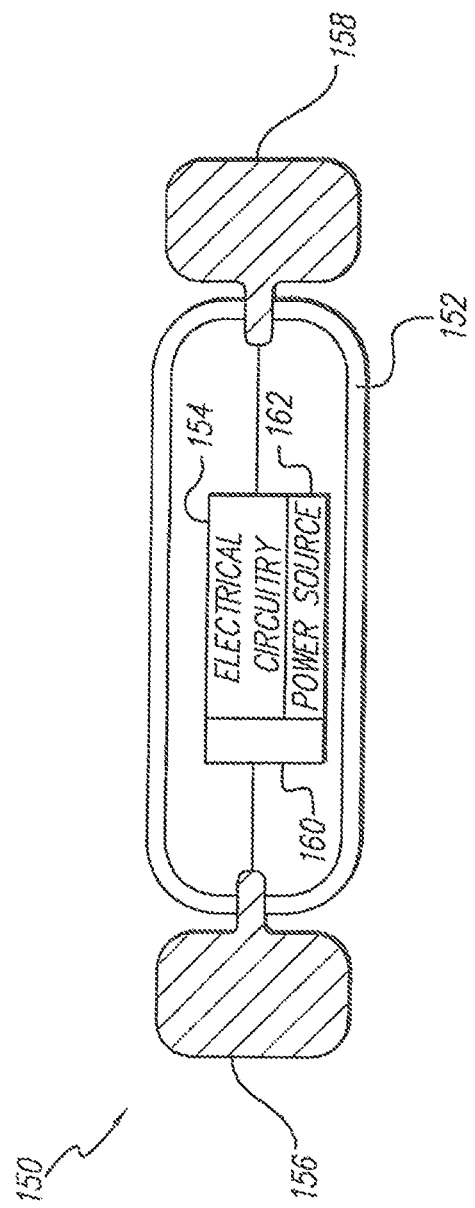
FIG. 4 illustrates an exemplary embodiment of a stimulation system of the present invention.

To treat some forms of urinary and/or bowel dysfunction, in accordance with the teachings of the present invention, a microminiature stimulator 150, such as a BION microstimulator, illustrated, e.g., in FIG. 4, is preferably implanted adjacent to one or more nerves containing a significant number of parasympathetic fibers, such as sacral nerves S2, S3, and S4. The sacral nerve roots lie within the spinal column, and a miniature implantable neurostimulator may be placed in the spinal column in an epidural location for stimulation of a sacral root(s). The sacral spinal nerves exit the sacral spinal column in the posterior pelvis, and a miniature neurostimulator may be placed at this point for stimulation of a sacral spinal nerve(s).

To treat some forms of urinary and/or bowel dysfunction, in accordance with the teachings of the present invention, a microminiature stimulator 150, such as a BION microstimulator, illustrated, e.g., in FIG. 4, is preferably implanted adjacent to one or more nerves containing a significant number of parasympathetic fibers, such as sacral nerves S2, S3, and S4. The sacral nerve roots lie within the spinal column, and a miniature implantable neurostimulator may be placed in the spinal column in an epidural location for stimulation of a sacral root(s). The sacral spinal nerves exit the sacral spinal column in the posterior pelvis, and a miniature neurostimulator may be placed at this point for stimulation of a sacral spinal nerve(s).

As shown in FIG. 4, microstimulator device 150 includes a narrow, elongated capsule 152 containing electronic circuitry 154 connected to electrodes 156 and 158, which pass through the walls of the capsule at either end. As detailed in the referenced patent publications, electrodes 156 and 158 comprise a stimulating electrode (to be placed close to the nerve) and an indifferent electrode (for completing the circuit). Other preferred configurations of microstimulator device 150 are possible, as is evident from the above-referenced patent publications.

Advantageously, a preferred implantable microstimulator 150 is sufficiently small to permit its placement near the structures to be stimulated. (As used herein, "adjacent" and "near" mean as close as reasonably possible to targeted tissue, including touching or even being positioned within the tissue, but in general, may be as far as about 150 mm from the target tissue.) In accordance with the present invention, a single microstimulator 150 may be implanted, or two or more microstimulators may be implanted to achieve greater stimulation of the targeted tissue, or for a longer period of time.

Capsule 152 preferably has a diameter no greater than about 4-5 mm, more preferably only about 3 mm, and most preferably less than about 3 mm. Capsule length is preferably no greater than about 25-35 mm, more preferably only about 20-25 mm, and most preferably less than about 20 mm. The shape of the microstimulator is preferably determined by the structure of the desired target, the surrounding area, and the method of insertion. A thin, elongated cylinder with electrodes at the ends, as shown in FIG. 4, is currently preferred, but other shapes, such as spheres, disks, or helical structures, are possible.

Microstimulator 150 is preferably implanted with a surgical insertion tool specially designed for the purpose, or is injected (e.g., via a hypodermic needle). Alternatively, device 150 may be implanted via conventional surgical methods, or may be inserted using other endoscopic or laparoscopic techniques. A more complicated surgical procedure may be required for purposes of fixing the microstimulator in place.

The external surfaces of stimulator 150 are advantageously composed of biocompatible materials. Capsule 152 is preferably made of glass, ceramic, or other material that provides a hermetic package that will exclude water vapor but permit passage of electromagnetic fields used to transmit data and/or power. Electrodes 156 and 158 are preferably made of a noble or refractory metal or compound, such as platinum, iridium, tantalum, titanium, titanium nitride, niobium, or alloys of any of these, in order to avoid corrosion or electrolysis which could damage the surrounding tissues and the device.

In one preferred embodiment of the instant invention, microstimulator 150 comprises two, leadless electrodes.

However, either or both electrodes 156 and 158 may alternatively be located at the ends of short, flexible leads as described in U.S. patent application Ser. No. 09/624,130, filed Jul. 24, 2000 (which claims priority to U.S. Provisional Patent Application No. 60/156,980, filed Oct. 1, 1999), which is incorporated herein by reference in its entirety. The use of such leads permits electrical stimulation to be directed more locally to specific tissue a short distance from the surgical fixation of the bulk of the implantable stimulator 150, while allowing elements of stimulator 150 to be located in a more surgically convenient site. This minimizes the distance traversed and the surgical planes crossed by the device and any lead(s). In a preferred embodiment, the leads are no longer than about 50 mm.

Microstimulator 150 preferably contains electronic circuitry 154 for receiving data and/or power from outside the body by inductive, radio-frequency (RF), or other electromagnetic coupling. In a preferred embodiment, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

In some preferred embodiments, microstimulator 150 advantageously includes a programmable memory 160 for storing a set(s) of stimulation and control parameters, if required. This feature allows stimulation and control parameters to be adjusted to settings that are safe and efficacious with minimal discomfort for each individual. Specific parameters may provide therapeutic advantages for various forms and severity of dysfunction. For instance, some patients may respond favorably to intermittent stimulation, while others may require continuous stimulation to treat their dysfunction.

In addition, stimulation parameters are typically chosen to target specific neural populations and to exclude others. For example, relatively low frequency neurostimulation (i.e., less than about 50-100 Hz) may have an excitatory effect on surrounding neural tissue, whereas relatively high frequency neurostimulation (i.e., greater than about 50-100 Hz) may have an inhibitory effect.

The preferred implantable stimulator 150 also includes a power source and/or power storage device 162. Possible power options, described in more detail below, include but are not limited to an external power source coupled to stimulator 150 via an RF link, a self-contained power source utilizing any means of generation or storage of energy (e.g., a primary battery, a rechargeable battery such as a lithium ion battery, an electrolytic capacitor, or a super- or ultra-capacitor), and if the self-contained power source is replenishable or rechargeable, means of replenishing or recharging the power source (e.g., an RF link, an optical link, a thermal link, or other energy-coupling link).

According to one embodiment of the invention, a microstimulator operates independently. According to another embodiment of the invention, a microstimulator operates in a coordinated manner with other microstimulator(s), other implanted device(s), or other device(s) external to the patient's body. For instance, a microstimulator may control or operate under the control of another implanted microstimulator(s), other implanted device(s), or other device(s) external to the patient's body. A microstimulator may communicate with other implanted microstimulators, other implanted devices, and/or devices external to a patient's body via, e.g., an RF link, an ultrasonic link, a thermal link, or an optical link. Specifically, a microstimulator may communicate with an external remote control (e.g., patient and/or physician programmer) that is capable of sending commands and/or data to a microstimulator and that is preferably capable of receiving commands and/or data from a microstimulator.

In order to help determine the strength of electrical stimulation required to produce the desired therapeutic effect, in one preferred embodiment, a patient's response to and/or need for treatment is sensed, such as changes in bladder condition. Thus, when implantable stimulator 150 is implanted, for example, near or adjacent a parasympathetic nerve(s), such as the pelvic splanchnic nerves 104, the signals traveling along the visceral sensory fibers of the nerve(s) may be sensed by a electroneurograph (ENG) built into microstimulator 150. In this example, the ENG would sense relatively low-frequency activity when the bladder is empty and relatively high-frequency activity when the bladder is full. Alternatively, a "microstimulator" dedicated to sensory processes may communicate with a microstimulator that provides the stimulation pulses. As described below, the implant circuitry 154 amplifies and transmits these sensed signals, which may be analog or digital. Other methods of determining the required stimulation include sensing bladder or sphincter pressure, a bladder or sphincter electromyograph (EMG) for sensing urinary dysfunction, a colon or anal sphincter EMG or pressure sensor for sensing bowel dysfunction, as well as other methods mentioned herein, and yet others that will be evident to those of skill in the art upon review of the present disclosure. The sensed information is preferably used to control electrical and/or control parameters in a closed-loop manner.

Figure 5:
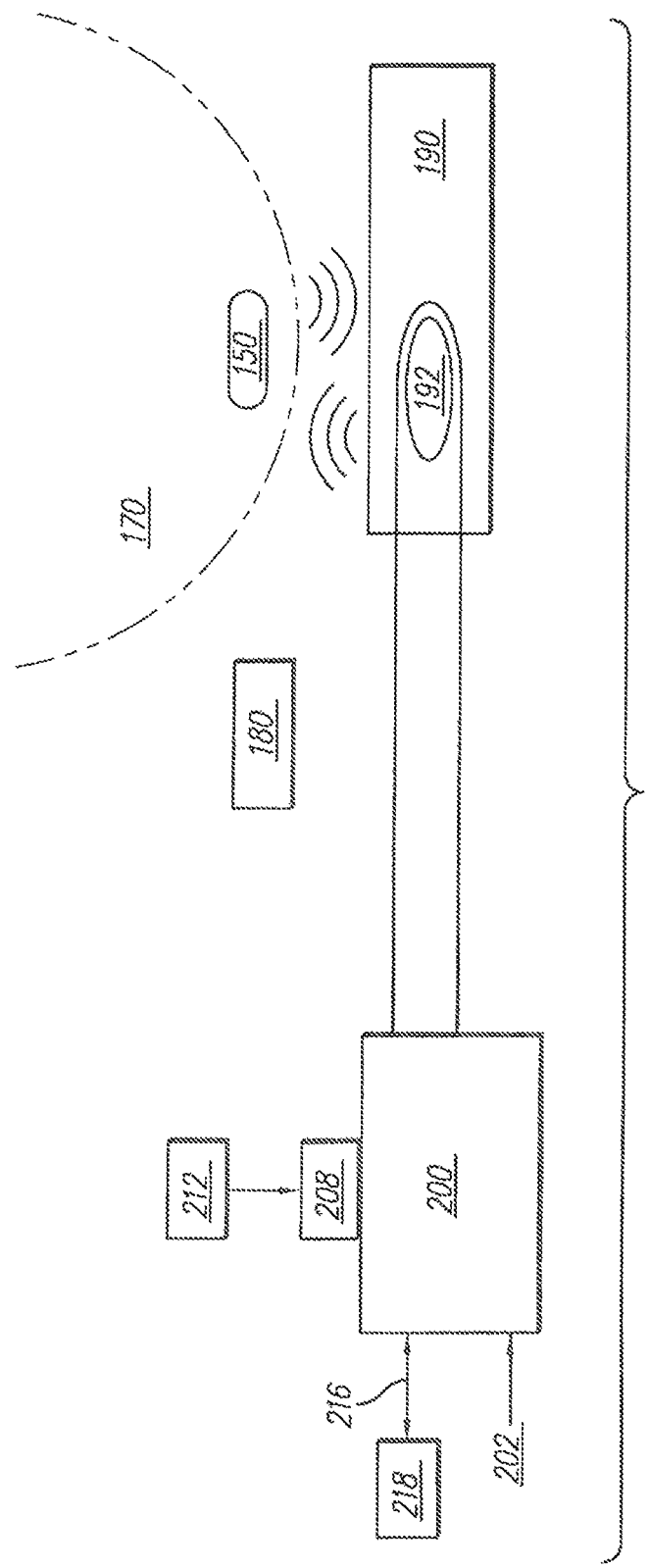
FIG. 5 illustrates preferred external components of the invention.

In operation, as illustrated in FIG. 5, the patient 170 turns the implantable stimulator 150 on and off by use of controller 180, which is preferably handheld. Implantable stimulator 150 is operated by controller 180 by any of various means, including sensing the proximity of a permanent magnet located in controller 180, or sensing RF transmissions from controller 180.

External components of one preferred embodiment for programming and/or providing power to the implantable stimulator 150 are also illustrated in FIG. 5. When it is required to communicate with the implanted stimulator 150, the patient 170 is positioned on or near external appliance 190, which appliance contains one or more inductive coils 192 or other means of communication (e.g., RF transmitter and receiver). External appliance 190 is connected to or is a part of external electronic circuitry appliance 200 which receives power 202 from a conventional power source. External appliance 200 contains manual input means 208, e.g., a keypad, whereby the patient 170 or a caregiver 212 can request changes in the stimulation parameters produced during the normal operation of the implantable stimulator 150. In this preferred embodiment, the manual input means 208 includes various electro-mechanical switches and/or visual display devices that provide the patient and/or caregiver with information about the status and prior programming of the implantable stimulator 150.

Alternatively or additionally, the external electronic appliance 200 is provided with an electronic interface means 216 for interacting with other computing means 218, such as by a serial interface cable or infrared link to a personal computer or to a telephone modem. Such interface means 216 thus permits a clinician to monitor the status of the implant and prescribe new stimulation parameters from a remote location.

The external appliance(s) may advantageously be embedded in a cushion, mattress cover, or garment. Other possibilities exist, including a belt or other structure that may be affixed to the patient's body or clothing.

Thus, it is seen that in accordance with the present invention, one or more external appliances are preferably provided to interact with microstimulator 150 to accomplish one or more of the following functions:

Function 1: If necessary, transmit electrical power from the external electronic appliance 200 via appliance 190 to the implantable stimulator 150 in order to power the device and/or recharge the power source/storage device 162. External electronic appliance 200 may include an automatic algorithm that adjusts stimulation parameters automatically whenever the implantable stimulator(s) 150 is/are recharged.

Function 2: Transmit data from the external appliance 200 via the external appliance 190 to the implantable stimulator 150 in order to change the operational parameters (e.g., electrical stimulation parameters) used by stimulator 150.

Function 3: Transmit sensed data indicating a need for treatment or in response to stimulation (e.g., nerve activity (e.g., ENG), muscle activity (e.g. EMG), impedance, pressure, electrical activity of the brain (e.g., EEG), or other activity) from implantable stimulator 150 to external appliance 200 via external appliance 190.

Function 4: Transmit data indicating state of the implantable stimulator 150 (e.g., battery level, stimulation settings, etc.) to external appliance 200 via external appliance 190.

By way of example, a treatment modality for a urinary dysfunction such as urinary incontinence is carried out according to the following sequence of procedures:

1. A stimulator 150 is implanted so that its electrodes 156 and 158 are located adjacent to one or more of the pelvic splanchnic nerves 104.
2. Using Function 2 described above (i.e., transmitting data) of external electronic appliance 200 and external appliance 190, stimulator 150 is commanded to produce a series of inhibitory (i.e., high frequency) electrical stimulation pulses with gradually increasing amplitude.
3. Set stimulator on/off period to an appropriate setting, e.g., five seconds on then five seconds off.
4. After each stimulation pulse, series of pulses, or some predefined interval, any neural activity is sensed, preferably by one or more electrodes 156 and 158 or via an ENG sensor. These responses are converted to data and telemetered out to external electronic appliance 200 via Function 3.
5. From the response data received at external appliance 200 from the implantable stimulator 150, or from other assessment, the stimulus threshold for obtaining a reflex response is determined and is used by a clinician acting directly 212 or by other computing means 218 to transmit the desired stimulation parameters to the implantable stimulator 150 in accordance with Function 2.
6. When patient 170 desires to e.g., initiate voiding, patient 170 employs handheld controller 180 to set the implantable stimulator 150 in a state where it delivers the prescribed stimulation pattern (e.g., switching from high frequency stimulation intended to block urination, to low frequency stimulation or no stimulation, thus prompting urination).
7. Patient 170 employs controller 180 to turn off stimulator 150, if desired.
8. Periodically, the patient or caregiver recharges the power source/storage device 162 of implantable stimulator 150 in accordance with Function 1 described above (i.e., transmit electrical power).

For the treatment of any of the various types and degrees of urinary dysfunction and bowel dysfunction, it may be desirable to modify or adjust the algorithmic functions performed by the implanted and/or external components, as well as the surgical approaches, in ways that would be obvious to skilled practitioners of these arts. For example, it may be desirable to employ more than one implantable stimulator 150, each of which could be separately controlled by means of a digital address. Multiple channels and/or multiple patterns of stimulation might thereby be programmed by the clinician and controlled by the patient in order to deal with bilateral, complex, or multiple dysfunctions such as may occur as a result of spinal cord injury and neurodegenerative disorders.

In one preferred embodiment, microstimulator 150, or a group of two or more microstimulators, is controlled via closed-loop operation. A need for and/or response to stimulation is sensed via microstimulator 150, or by an additional microstimulator (which may or may not be dedicated to the sensing function), or by another implanted or external device. If necessary, the sensed information is transmitted to microstimulator 150. Preferably, the stimulation parameters used by microstimulator 150 are automatically adjusted based on the sensed information. Thus, the stimulation parameters are adjusted in a closed-loop manner to provide stimulation tailored to the response to stimulation.

For instance, in one embodiment of the present invention, a first and second "stimulator" are provided. The second "stimulator" periodically (e.g. once per minute) records a level of e.g., neural activity or of pressure in the bladder, which it transmits to the first stimulator. The first stimulator uses the sensed information to adjust stimulation parameters according to an algorithm programmed, e.g., by a physician. For example, amplitude of stimulation may be increased in response to increased bladder pressure. More preferably, one "microstimulator" performs both the sensing and current generating functions.

Figure 6:
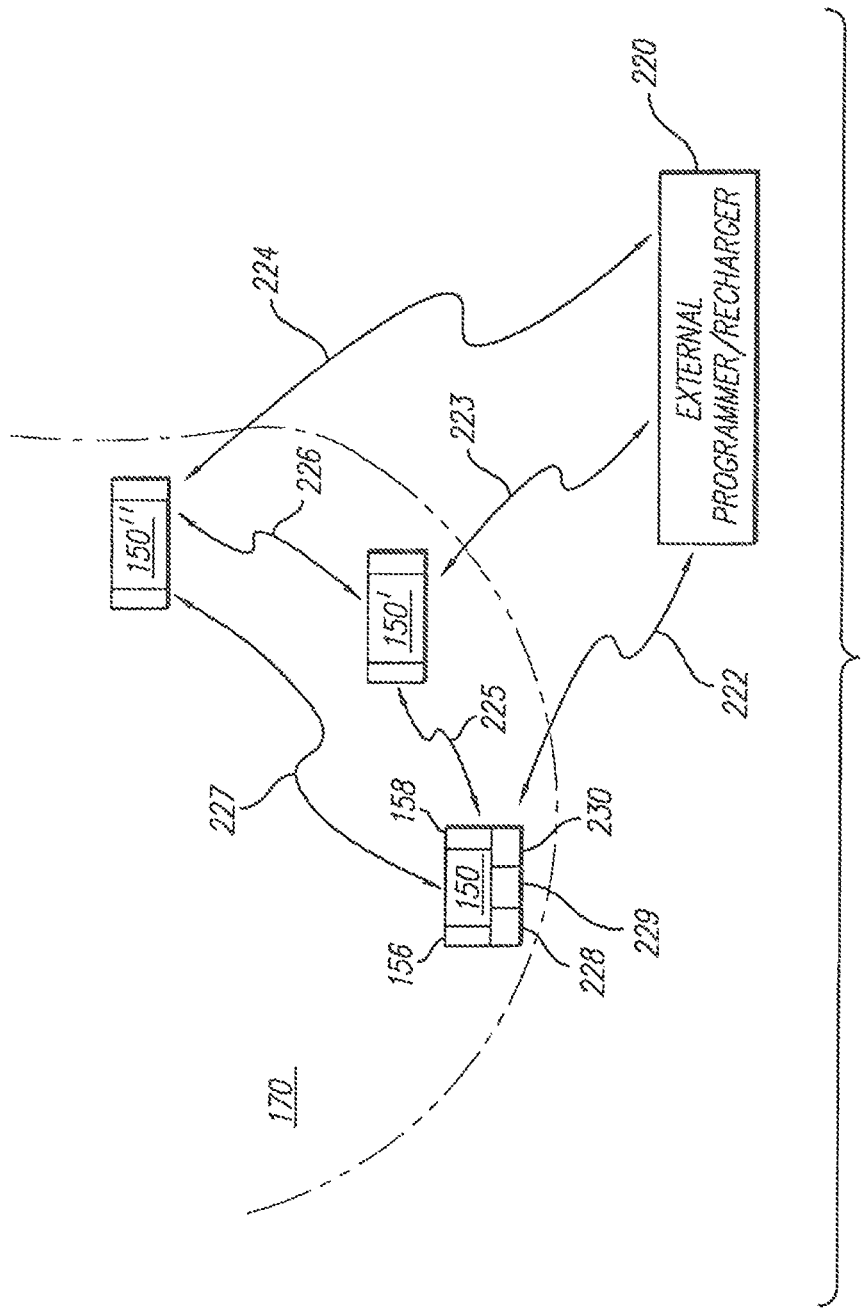
FIG. 6 depicts a system of implantable devices that communicate with each other and/or with external control/programming devices.

For example, as seen in FIG. 6, a first microstimulator 150, implanted beneath the skin of the patient 170, provides electrical stimulation via electrodes 156 and 158 to a first location; a second microstimulator 150' provides electrical stimulation to a second location; and a third microstimulator 150" provides electrical stimulation to a third location. As mentioned earlier, the implanted devices may operate independently or may operate in a coordinated manner with other similar implanted devices, other implanted devices, or other devices external to the patient's body, as shown by the control lines 222, 223 and 224 in FIG. 6. That is, in accordance with one embodiment of the invention, the external controller 220 controls the operation of each of the implanted microstimulators 150, 150' and 150". According to another embodiment of the invention, an implanted device, e.g. microstimulator 150, may control or operate under the control of another implanted device(s), e.g. microstimulator 150' and/or microstimulator 150". That is, a device made in accordance with the invention may communicate with other implanted stimulators, other implanted devices, and/or devices external to a patient's body, e.g., via an RF link, an ultrasonic link, a thermal link, or an optical link. Specifically, as illustrated in FIG. 6, microstimulator 150, 150', and/or 150", made in accordance with the invention, may communicate with an external remote control (e.g., patient and/or physician programmer 220) that is capable of sending commands and/or data to implanted devices and that is capable of receiving commands and/or data from implanted devices.

Microstimulators made in accordance with the invention further incorporate, in one embodiment, first sensing means 228 for sensing therapeutic effects, clinical variables, or other indicators of the state of the patient, such as ENG. The stimulators additionally or alternatively incorporate second means 229 for sensing changes in bladder condition, bladder pressure, internal urethral sphincter pressure, external urethral sphincter pressure, colon pressure, anal sphincter pressure, bladder EMG, internal urethral sphincter EMG, external urethral sphincter EMG, colon EMG, and/or anal sphincter EMG. The stimulators additionally or alternatively incorporate third means 230 for sensing electrical current levels and waveforms supplied by another source of electrical energy. Sensed information may then be used to control the parameters of the stimulator(s) in a closed loop manner, as shown by control lines 225, 226, and 227. Thus, the sensing means may be incorporated into a device that also includes electrical stimulation means, or the sensing means (that may or may not have stimulating means), may communicate the sensed information to another device(s) with stimulating means.

While a microstimulator may also incorporate means of sensing urinary and/or bowel dysfunction, e.g., via an ENG or a bladder, colon, or sphincter pressure sensor or EMG, it may alternatively or additionally be desirable to use a separate or specialized implantable device to sense and telemeter physiological conditions/responses in order to adjust stimulation parameters. This information may then be transmitted to an external device, such as external appliance 220, or may be transmitted directly to implanted stimulator(s) 150. However, in some cases, it may not be necessary or desired to include a sensing function or device, in which case stimulation parameters are determined and refined, for instance, by patient feedback.

As described earlier, microstimulator 150 includes means to stimulate intermittently or continuously. Specific stimulation parameters provide therapeutic advantages for various forms of dysfunction.

According to one therapeutic alternative, the dysfunction is treated with decreased excitement of targeted parasympathetic nerve fibers, such as the sacral root(s) and/or sacral spinal nerve(s), e.g., from S2 and/or S4, and/or more preferably from S3. High-frequency electrical stimulation (e.g., greater than about 50-100 Hz) is likely to produce such inhibition. Depending on the specific condition of a patient, this therapy is most likely to provide relief to patients with, e.g., urgency, frequency, and/or urinary incontinence, especially urinary urge incontinence. Alternatively or additionally, the patient may be treated with decreased excitement of other parasympathetic nerves, e.g., pelvic splanchnic nerves 104 or its branches to, e.g., the inferior hypogastric, prostatic, vesical, and/or uterovaginal plexuses.

According to another therapeutic alternative, the dysfunction is treated with increased excitement of targeted parasympathetic nerve fibers, such as the sacral root(s) and/or sacral spinal nerve(s), e.g., from S2 and/or S4, and/or more preferably from S3. Low-frequency electrical stimulation (e.g., less than about 50-100 Hz) is likely to produce such excitement. More particularly, parasympathetic tissue has been demonstrated to have a maximal response to stimulation of 20-35 Hz, with a decrease in response at frequencies above and below this range. This therapy is most likely to provide relief to patients, e.g., lacking or with impaired ability to initiate urinary voiding (i.e., suffering from urinary retention). Alternatively, the dysfunction is treated with increased excitement of other parasympathetic nerves, e.g., pelvic splanchnic nerves 104 or its branches to, e.g., the inferior hypogastric, prostatic, vesical, and/or uterovaginal plexuses.

According to yet another therapeutic alternative, the dysfunction is treated with increased excitement of targeted sympathetic nerve fibers, such as the thoracic and/or lumbar root(s) and/or spinal nerve(s), e.g., from one or more of T1 through T12, and more preferably from L1 and/or L2. Low-frequency electrical stimulation (e.g., less than about 50-100 Hz) is likely to produce such excitement. Depending on the specific condition of a patient, this therapy is most likely to provide relief to patients with, e.g., urgency, frequency, and/or urinary incontinence, especially urinary urge incontinence. Alternatively, the dysfunction is treated with increased excitement of other sympathetic nerves, e.g., lumbar splanchnic nerves 114 or its branches.

According to another therapeutic alternative, the dysfunction is treated with decreased excitement of targeted sympathetic nerve fibers, such as the thoracic and/or lumbar root(s) and/or spinal nerve(s), e.g., from one or more of T1 through T12, and more preferably from L1 and/or L2. High-frequency electrical stimulation (e.g., greater than about 50-100 Hz) is likely to produce such inhibition. This therapy is most likely to provide relief to patients, e.g., lacking or with impaired ability to initiate urinary voiding (i.e., suffering from urinary retention). Alternatively, the dysfunction is treated with decreased excitement of other sympathetic nerves, e.g., lumbar splanchnic nerves 114 or its branches.

Other embodiments of the invention address bowel dysfunction. For instance, according to one alternative, a dysfunction such as fecal incontinence is treated with decreased excitement of targeted parasympathetic nerves, such as the sacral root(s) and/or sacral spinal nerves from S2, S3 and/or S4, and/or the pelvic splanchnic nerves 104 and/or its branches, e.g., the rectal plexus. High-frequency electrical stimulation (e.g., greater than about 50-100 Hz) is likely to produce such inhibition. According to another alternative, bowel dysfunction such as the inability to or with impaired ability to initiate defecation (i.e., fecal retention) is treated with increased excitement of one or more of these parasympathetic nerves. Low-frequency electrical stimulation (e.g., less than about 50-100 Hz) is likely to produce such excitement.

An alternative therapy for patients experiencing bowel dysfunction such as fecal incontinence is increased excitement of targeted sympathetic nerves, such as the thoracic and/or lumbar root(s) and/or spinal nerves from T9, T10, T11, T12, L1, and/or L2, and/or greater splanchnic nerve 108, lesser splanchnic nerve 110, least splanchnic nerve 112, and/or lumbar splanchnic nerves 114, and/or their branches. Low-frequency electrical stimulation (e.g., less than about 50-100 Hz) is likely to produce such excitement. According to another alternative, bowel dysfunction such as the inability to or with impaired ability to initiate defecation (i.e., fecal retention) is treated with decreased excitement of one or more of these sympathetic nerves. High-frequency electrical stimulation (e.g., greater than about 50-100 Hz) is likely to produce such inhibition.

Large diameter fibers (e.g., A-$\alpha$ and/or A-$\beta$ fibers) respond to relatively lower current density stimulation vis-á-vis small diameter fibers (e.g., A-$\delta$ and/or C fibers). Thus, an additional alternative provides stimulation of, e.g., the S3 dorsal root with a relatively low stimulation current amplitude. This stimulation is thus more likely to excite relatively large diameter fibers responsible for the sensations of touch and position sense, and is unlikely to activate relatively small diameter fibers responsible for pain and thermal sensation. Such stimulation is likely to activate the reflex that inhibits bladder contraction for the treatment of urinary incontinence while avoiding any painful sensations.

In yet another alternative, sensing means described earlier may be used to orchestrate first the activation of microstimulator(s) targeting nerves that inhibit voiding, and then, when appropriate, the microstimulator(s) targeting nerves that cause voiding.

While the invention herein disclosed has been described by means of specific embodiments and applications thereof, numerous modifications and variations could be made thereto by those skilled in the art without departing from the scope of the invention set forth in the claims.

The invention claimed is:

1. A method of operating an implantable stimulator to treat a urinary dysfunction, the method comprising:
   implanting at least one implantable stimulator with at least two electrodes positioned adjacent to at least one target nerve comprising at least one of a thoracic root; a thoracic spinal nerve; a lumbar root; a lumbar spinal nerve; a hypogastric nerve; a superior hypogastric nerve plexus; an inferior hypogastric nerve plexus; a greater splanchnic nerve; a lesser splanchnic nerve; a least splanchnic nerve; a lumbar splanchnic nerve; or branches thereof;
   providing stimulation parameters to the at least one implantable stimulator;
   generating stimulation pulses in accordance with the stimulation parameters; and
   delivering the stimulation pulses to the at least one target nerve in order to treat at least one of urinary urgency, urinary frequency, urinary retention, or urinary incontinence.

2. The method of claim 1, wherein the target nerve comprises at least one parasympathetic nerve.

3. The method of claim 2, wherein the parasympathetic nerve comprises the inferior hypogastric nerve plexus.

4. The method of claim 1, wherein the target nerve comprises at least one sympathetic nerve.

5. The method of claim 4, wherein the at least one sympathetic nerve comprises one or more of a thoracic root, a thoracic spinal nerve, a lumbar root, a lumbar spinal nerve, the hypogastric nerves, the superior hypogastric plexus, the inferior hypogastric plexus, the greater splanchnic nerve, the lesser splanchnic nerve, the least splanchnic nerve, the lumbar splanchnic nerves, and their branches.

6. The method of claim 1, further comprising:
   sensing at least one physical condition of a patient; and
   determining the stimulation parameters based upon the at least one sensed physical condition.

7. The method of claim 6, wherein sensing at least one physical condition of a patient comprises sensing at least one of a bladder condition, bladder pressure, internal urethral sphincter pressure, external urethral sphincter pressure, bladder electromyography (EMG), internal urethral sphincter EMG, or external urethral sphincter EMG.

8. The method of claim 1, wherein providing stimulation parameters comprises transmitting the stimulation parameters from at least one external appliance.

9. The method of claim 1, wherein the stimulation pulse is an inhibitory stimulation pulse that inhibits parasympathetic or sympathetic input.

10. The method of claim 9, further comprising
    generating excitatory stimulation pulses with said at least one stimulator in accordance with the stimulation parameters; and
    delivering the excitatory stimulation pulses to nerves and tissue adjacent to the at least two electrodes in order to treat said urinary dysfunction.

11. The method of claim 1, further comprising providing and implanting more than one implantable stimulator, wherein the implantable stimulators operate in a coordinated manner.

12. A method of operating an implantable stimulator to treat urinary incontinence, the method comprising:
    implanting at least one implantable stimulator with at least two electrodes positioned adjacent to at least one target nerve originating at the thoracolumbar part of the spinal cord;
    providing first stimulation parameters to the at least one implantable stimulator;
    generating first stimulation pulses in accordance with the first stimulation parameters;
    delivering the first stimulation pulses to the at least one target nerve in order to block urination;
    receiving a signal from a controller to initiate urination;
    providing second stimulation parameters to the at least one implantable stimulator;
    generating second stimulation pulses in accordance with the second stimulation parameters; and
    delivering the second stimulation pulses to the at least one target nerve in order to initiate urination.

13. The method of claim 12, wherein receiving a signal from a controller comprises receiving a signal from a controller operated by a patient within whom the at least one implantable stimulator is implanted.

14. The method of claim 12, further comprising, after initiating urination and completing urination, returning to the generating of the first stimulation pulses and the delivering of the first stimulation pulses to block urination.

* * * * *